(12) United States Patent
He et al.

(10) Patent No.: US 11,141,724 B2
(45) Date of Patent: Oct. 12, 2021

(54) METHOD FOR EFFICIENTLY CATALYZING FURFURAL TO PREPARE CYCLOPENTANONE, AND CATALYST AND PREPARATION METHOD THEREFOR

(71) Applicant: BEIJING UNIVERSITY OF CHEMICAL TECHNOLOGY, Beijing (CN)

(72) Inventors: Jing He, Beijing (CN); Yanru Zhu, Beijing (CN); Zhe An, Beijing (CN)

(73) Assignee: BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 0 days.

(21) Appl. No.: 16/967,400

(22) PCT Filed: Dec. 24, 2018

(86) PCT No.: PCT/CN2018/122982
§ 371 (c)(1),
(2) Date: Aug. 4, 2020

(87) PCT Pub. No.: WO2019/214247
PCT Pub. Date: Nov. 14, 2019

(65) Prior Publication Data
US 2021/0213439 A1 Jul. 15, 2021

(30) Foreign Application Priority Data
May 8, 2018 (CN) .......................... 201810430384.9

(51) Int. Cl.
| | |
|---|---|
| *C07C 45/59* | (2006.01) |
| *B01J 37/00* | (2006.01) |
| *B01J 37/18* | (2006.01) |
| *B01J 23/89* | (2006.01) |
| *B01J 35/00* | (2006.01) |
| *B01J 37/06* | (2006.01) |
| *B01J 37/04* | (2006.01) |
| *B01J 37/08* | (2006.01) |

(52) U.S. Cl.
CPC ........... *B01J 37/18* (2013.01); *B01J 23/8953* (2013.01); *B01J 35/006* (2013.01); *B01J 37/009* (2013.01); *B01J 37/04* (2013.01); *B01J 37/06* (2013.01); *B01J 37/08* (2013.01); *C07C 45/59* (2013.01)

(58) Field of Classification Search
CPC ......... C07C 45/59; B01J 37/18; B01J 37/009; B01J 37/08
See application file for complete search history.

(56) References Cited

U.S. PATENT DOCUMENTS

2009/0054703 A1  2/2009  Kourtakis

FOREIGN PATENT DOCUMENTS

| CN | 105130746 A | 12/2015 |
| CN | 105854883 A | 8/2016 |
| CN | 107365287 A | 11/2017 |
| CN | 108855130 A | 11/2018 |

OTHER PUBLICATIONS

Barrabes,etc. Hydrodechlorination of trichloroethylene on noble metal promoted Cu-hydrotalcite. Mar. 3, 2009 ,Journal of Catalysis, vol. 263.

*Primary Examiner* — Sikarl A Witherspoon
(74) *Attorney, Agent, or Firm* — Leonid Kisselev

(57) ABSTRACT

A method for efficiently catalyzing furfural to prepare cyclopentanone, and a catalyst and preparation method therefor, are disclosed, in the field of biomass catalytic conversion. The catalyst comprises uniformly dispersed metal active center nanoparticles and oxides obtained by LDHs calcination. The metal active center is single atom Pt/Cu alloy; the LDHs is used as a precursor to prepare a Cu-containing catalyst precursor; after a reduction in $H_2$ atmosphere, small amount of $Pt^{2+}$ is used for reacting with the Cu-containing catalyst precursor to obtain a monoatomic Pt/Cu catalyst; said catalyst is used to catalyze hydrogenation of an aqueous phase of furfural to prepare cyclopentanone, wherein the reaction temperature is 120-250° C., the reaction pressure is 0.1-5 MPa, the reaction time is 0.5-24 hours, and the reaction solvent is ultrapure water. Low-cost and efficient, the catalyst catalyzes the hydrogenation of an aqueous phase of furfural to prepare cyclopentanone. When the reaction is carried out at 160° C. at an initial pressure of 0.1 MPa for 1 hour, the furfural is completely converted, and the yield of the cyclopentanone reaches 99%.

20 Claims, No Drawings

METHOD FOR EFFICIENTLY CATALYZING FURFURAL TO PREPARE CYCLOPENTANONE, AND CATALYST AND PREPARATION METHOD THEREFOR

CROSS REFERENCE TO RELATED APPLICATION

This application is a national stage application of International application number PCT/CN2018/122982, filed Dec. 24, 2018, titled "Method for efficiently catalyzing furfural to prepare cyclopentanone, and catalyst and preparation method therefor," which claims the priority benefit of Chinese Patent Application No. 201810430384.9, filed on May 8, 2018, which is hereby incorporated by reference in its entirety.

TECHNICAL FIELD

The invention relates, in general, to the field of biomass catalysis, and in particular to a catalyst for efficiently producing cyclopentanone by furfural conversion and its' preparation method thereof, and a method for efficiently producing cyclopentanone.

BACKGROUND

Furfural can be produced from pentose, a renewable biomass resource through acid-catalyzed dehydration. It is one of the important biomass platform molecules and can be converted into high-value-added biofuels and fine chemicals. Catalytic hydrogenation of furfural is a series of important reactions, and products such as furfuryl alcohol, tetrahydrofurfuryl alcohol, 2-methylfuran and cyclopentanone can be obtained. Because the process of hydrogenation of furfural involves hydrogenation of C=O and C=C bonds, the breaking of C—C and C—O bonds, and so on, it is very challenging to obtain the desired target product with high selectivity.

Cyclopentanone is a versatile fine chemical product and an important intermediate in various chemical synthesis. It can be used to synthesize drugs, fungicides, rubber chemicals as well as spices and perfume chemicals. Currently in industry, petroleum routes are used for cyclopentanone production, mainly by liquid phase oxidation of nitrous oxide cyclopentene, or by gas phase cyclization of 1,6-hexanediol or adipic acid. In comparison, the preparation of cyclopentanone from renewable biomass or platform molecules conforms to the current trend of green and clean chemical processes and is of great significance. Recently, a route of converting furfural to cyclopentanone has been reported, which may be used as a raw material to replace unsustainable fossil fuels.

Furfural is the product of acid-catalyzed dehydration of pentose in aqueous phase. The process of separating furfural from formed aqueous solution increases its production cost. Therefore, it is very beneficial to use aqueous furfural as a raw material for producing chemicals and fuels. Recently, Hronec et al. reported a new method for the preparation of cyclopentanone by hydrogenation of furfural and furfuryl alcohol rearrangement in water. They found that some metal catalysts (such as Pt/C, Pd—Cu/C and Ni-based catalysts) exhibited good selective conversion of furfural or furfuryl alcohol to cyclopentanone. In other reports, Ni—Cu/SBA-15, Cu—Co, ZnAl oxide supported Cu, Ru/MIL-101 and other catalytic systems have been developed for the preparation of cyclopentanone in the furfural aqueous phase.

Although some pioneering work has been done in this field, the research is still in its infancy. Due to the low solubility of gas in water and the transmission resistance between multiphase interfaces, gas-liquid-solid phase heterogeneous catalytic reactions often encounter problems of low catalytic efficiency. The efficient conversion of furfural to cyclopentanone under mild conditions remains a challenge.

SUMMARY

One objective the present invention is to provide a catalyst for producing cyclopentanone by efficiently catalyzing the conversion of furfural and a preparation method thereof, and a method for efficiently catalyzing the conversion of furfural to prepare cyclopentanone, which can efficiently catalyze the conversion of furfural to cyclopentanone under moderate reaction conditions.

The present disclosure provides a catalyst for efficiently catalyzing the conversion of furfural to prepare cyclopentanone. The catalyst comprises a uniformly dispersed metal active center nanoparticles and an oxide obtained by calcination of Cu-containing layered double hydroxides (LDHs), the metal active center of the catalyst is single atom Pt/Cu alloy, that is, Pt atom is loaded in situ onto the surface of nanotwined Cu particle.

Preferably, the Cu content of the metal active center in the catalyst is 5-30 wt %, the Pt content is 0.01-3 wt %, and the particle size of the single atom Pt/Cu alloy in the metal active center is 2-10 nm.

More preferably, the Cu content of the metal active center is 8-20% by weight, the Pt content is 0.05-1% wt %, and the particle size of the single atom Pt/Cu alloy particles is 2-10 nm.

The present disclosure also provides a method for preparing the above-mentioned catalysts for efficient conversion of furfural to prepare cyclopentanone. The preparation method includes: using LDHs as a precursor to obtain a Cu-containing catalyst precursor, which is subsequently reduced in an $H_2$ atmosphere, and subsequently $Pt^{2+}$ is introduced to react with the Cu-containing catalysts precursor, the reaction product is washed and dried to obtain the catalyst containing the single atom Pt/Cu alloy metal active center and the oxides as support.

Preferably, the preparation of the Cu-containing catalyst precursor using LDHs as a precursor is performed as the following: Cu-containing hydrotalcite is reduced in a $H_2$ atmosphere, the reduction temperature is controlled at 400° C. to 650° C., and the reduction time is controlled at 5 minutes to 6 hours, to generate the Cu-containing catalyst precursor.

In the present disclosure, the divalent cation of LDHs lattice of the Cu-containing LDHs precursor is selected from $Zn^{2+}$ or/and $Mg^{2+}$, the trivalent cation is selected from $Al^{3+}$, and the metal active center ion inside the lattice is $Cu^{2+}$.

In the present disclosure, the molar ratio between the divalent cation $Zn^{2+}$ or/and $Mg^{2+}$ of the LDHs lattice and the metal active center ion $Cu^{2+}$ inside the lattice is (0-10):1, the divalent cation $Zn^{2+}$ or/and $Mg^{2+}$ of the lattice is not 0, and the molar ratio between all divalent metal cations $Zn^{2+}$, $Mg^{2+}$ and $Cu^{2+}$ and all trivalent metal cations in the LDHs laminate is in the range of (2-5):1.

Further preferably, during the preparation of Cu-containing catalyst precursor using LDHs as the precursor, the LDHs precursor also contains tetravalent cations in the LDHs lattice, the tetravalent cations are selected as $Zr^{4+}$, the molar ratio of $Zr^{4+}$ to the trivalent cation $Al^{3+}$ is (0.1-1):1, such as 0.5:1.

The preparation method of the catalyst includes the steps of: preparing Cu-containing catalyst precursor by reducing LDHs precursor in a $H_2$ atmosphere, with the reduction temperature being controlled at 400° C. to 650° C., and the reduction time being controlled at 5 minutes to 6 hours to obtain the Cu-containing catalyst precursor, seal the Cu-containing catalyst precursor with de-oxygenated deionized water; under stirring and $N_2$ protection, a $Pt^{2+}$ solution is added dropwise to the liquid-sealed the Cu-containing catalyst precursor, and let react at 90-120° C. for 1-3 hours, separate, wash, and dry to obtain the single atom Pt/Cu alloy catalyst.

The present disclosure also provides a method for efficiently catalyzing the conversion of furfural to prepare cyclopentanone. Use the above-mentioned catalyst or catalyst prepared by the above-mentioned preparation method to catalyze the furfural reaction. The $Pt^{2+}$ reaction conditions are: reaction temperature is 120-250° C., reaction pressure is 0.1-5 MPa, reaction time is 0.5 to 24 hours, and the reaction solvent is ultrapure water.

In a preferred embodiment of the present invention, a method is disclosed for producing cyclopentanone using a single-atom Pt/Cu alloy catalyst catalyzing furfural: using hydrogen to replace the air in a reactor and filling appropriate pressure, the mass fraction of substrate furfural to 1-20 wt %, using the Cu-containing catalyst, reaction temperature is 120-250° C., reaction pressure is 0.1-5 MPa, reaction time is 0.5 to 24 hours, and the reaction solvent is ultrapure water.

As disclosed, the Pt/Cu-containing catalyst is composed of uniformly dispersed Pt/Cu alloy nanoparticles and an oxide as supports obtained by calcination of LDHs, the metal active center is single atom Pt/Cu alloy; preferably, the Cu content of the catalyst metal active center is 5-30 wt %, Pt content is 0.01-3 wt %, and the particle size of active metal center is 2-20 nm.

Preferably, the preparation of a single atom Pt/Cu alloy catalyst includes the steps of: using bimetallic composite hydroxide, also known as LDHs, as the precursor system, selecting $Zn^{2+}$ or $Mg^{2+}$ as the divalent cation of LDHs lattice, selecting $Al^{3+}$ as trivalent cation, the metal active center ion inside the lattice is $Cu^{2+}$, wherein the molar ratio of the divalent cation of LDHs lattice to the metal active center ion $Cu^{2+}$ is (0-10):1. The molar ratio between all divalent cations on LDHs laminate and all trivalent cations is (2-5):1, the LDHs precursor is reduced in a $H_2$ atmosphere, the reduction temperature is controlled at 400-550° C., the reduction time is controlled at 5 minutes to 6 hours, to generate the Cu-containing catalyst precursor. A small amount of $Pt^{2+}$ is added to react with the Cu-containing catalyst precursor, and undergoes reduction in a $H_2$ atmosphere, the monoatomic Pt/Cu catalyst is thus obtained. Furthermore, selecting $Zr^{4+}$ as tetravalent cations to enter the LDHs lattice.

The invention has the following advantages:

1. The catalyst of the present disclosure is composed of uniformly dispersed metal nanoparticles Pt/Cu alloy and carrier zinc aluminum composite oxide. The catalyst is produced by reduction of LDHs precursor. The selected divalent cations in LDHs lattice are $Zn^{2+}$ or $Mg^{2+}$, and the selected trivalent cation is $Al^{2+}$, the molar ratio of $M^{2}\pm/M^{3+}$ is 2-5, the molar ratio of $M^{2+}/Cu^{2+}$ is (0-10). The metal cation ratio and composition of LDHs lattice can be adjusted to control the metal active center composition of the catalyst. The in situ reduction the Cu-containing LDHs generates a uniformly dispersed Cu-based catalyst, Pt is subsequently loaded onto the Cu-based catalyst to obtain a Pt/Cu loaded catalyst. Using the adjustable characteristics of metal ion ratio and composition of LDHs lattice, a highly dispersed loaded single atom Pt/Cu catalyst with adjustable loading and composition is prepared to catalyze the conversion of furfural to cyclopentanone, and the yield of cyclopentanone reaches 99%.

2. The reaction conditions are mild and the energy consumption is low. The reaction can convert furfural completely at 160° C. and 0.1 MPa initial pressure.

3. The reaction is easy to operate and can finish in a sealed reactor.

DETAILED DESCRIPTION OF THE PREFERRED EMBODIMENTS

The present disclosure will be further described below with the preferred embodiment, but the present invention is not limited to the following examples.

Embodiment 1

Step A: $Cu(NO_3)_2 \cdot 3H_2O$ (14 mmol), $Zn(NO_3)_2 \cdot 6H_2O$ (42 mmol), $Al(NO_3)_3 \cdot 9H_2O$ (12 mmol), and $ZrO(NO_3)_2 \cdot 6H_2O$ (6 mmol) are dissolved in 200 mL deionized water as solution A, NaOH (0.156 mol), $Na_2CO_3$ (0.024 mol) are dissolved into 200 mL deionized water as solution B. Subsequently, at a constant pH (10.0), solutions A and B are simultaneously added dropwise to a four-necked flask containing 200 mL of deionized water. After crystallization at 65° C. for 12 hours, the solid is filtered, washed with deionized water several times until the filtrate is neutral, and then dried overnight at 80° C. to obtain a CuZnAlZr-LDHs sample.

Step B: add the CuZnAlZr-LDHs synthesized in step A into a tube furnace, under $H_2$ atmosphere (40 mL $min^{-1}$), raise the temperature from room temperature to 450° C. at a rate of 2° C. $min^{-1}$ and maintained for 2 hours, to obtained Cu—Zn(Al)(Zr)O. Take 1 g reduced Cu—Zn(Al)(Zr)O, liquid-seal it with 5 mL deionized water with oxygen removed, pour it into a round bottom flask, and add $Pt^{2+}$ solution under vigorous stirring and $N_2$ protection. After that, replacement reaction is proceeded with a reflux condenser at 100° C. under vigorous stirring for 2 hours. The mud-like substance separated by centrifugation is washed three times with deionized water, and dried in vacuum at 40° C. for 24 hours.

A Pt/Cu—Zn(Al)(Zr)O catalyst is thus prepared. The actual loading of Pt is 0.1%, the actual loading of Cu is 11%, and particle size of the metal center is 2-20 nm.

The Pt/Cu—Zn(Al)(Zr)O catalyst obtained in embodiment 1 is used to catalyze the furfural hydro-conversion. Add 0.5 g of furfural, 0.03 g catalyst, 10 mL ultrapure water to the lining of autoclave, install the autoclave, fill $H_2$ from the air inlet, replace the air in autoclave 5 times, then fill with 0.1 MPa $H_2$, seal the autoclave. The autoclave is heated to a preset temperature. The pressure is about 0.5 MPa at 160° C., and the timing is started. The reaction is continued for 10 hours. During the process, $H_2$ is continuously replenished to 0.5 MPa. After the reaction is completed, it is cooled to room temperature, liquid in the reactor is centrifuged, and product is quantitatively analyzed by GC. The furfural conversion rate on Pt/Cu—Zn(Al)(Zr)O catalyst is measured to be 100%, and the selectivity to cyclopentanone is 99%.

Embodiment 2

Step A: $Cu(NO_3)_2 \cdot 3H_2O$ (10 mmol), $Zn(NO_3)_2 \cdot 6H_2O$ (46 mmol), $Al(NO_3)_3 \cdot 9H_2O$ (12 mmol), and $ZrO(NO_3)_2 \cdot 6H_2O$ (6 mmol) are dissolved in 200 mL deionized water as solution A, NaOH (0.156 mol) and $Na_2CO_3$ (0.024 mol) are dissolved into 200 mL deionized water as solution B. Subsequently, at a constant pH (10.0), solutions A and B are simultaneously added dropwise to a four-necked flask containing 200 mL of deionized water. After crystallization at 65° C. for 12 hours, the solid is filtered, washed with deionized water several times until the filtrate is neutral, and then dried overnight at 80° C. to obtain a CuZnAlZr-LDHs sample.

Step B: add the CuZnAlZr-LDHs synthesized in step A into a tube furnace, under $H_2$ atmosphere (40 mL min$^{-1}$), raise the temperature from room temperature to 450° C. at a rate of 2° C. min$^{-1}$ and maintained for 2 hours, to obtained Cu—Zn(Al)(Zr)O. Take 1 g reduced Cu—Zn(Al)(Zr)O, liquid-seal it with 5 mL deionized water with oxygen removed, pour it into a round bottom flask, and add $Pt^{2+}$ solution under vigorous stirring and $N_2$ protection. After that, replacement reaction is proceeded with a reflux condenser at 100° C. under vigorous stirring for 2 hours. The mud-like substance separated by centrifugation is washed three times with deionized water, and dried in vacuum at 40° C. for 24 hours.

A Pt/Cu—Zn(Al)(Zr)O catalyst is thus prepared. The actual loading of Pt is 0.1%, the actual loading of Cu is 8%, and particle size of the metal center is 2-20 nm.

The Pt/Cu—Zn(Al)(Zr)O catalyst obtained in embodiment 2 is used to catalyze the furfural hydro-conversion. Add 0.5 g of furfural, 0.03 g catalyst, 10 mL ultrapure water to the lining of autoclave, install the autoclave, fill $H_2$ from the air inlet, replace the air in autoclave 5 times, then fill with 0.1 MPa $H_2$, seal the autoclave. The autoclave is heated to a preset temperature. The pressure is about 0.5 MPa at 160° C., and the timing is started. The reaction is continued for 10 hours. During the process, $H_2$ is continuously replenished to 0.5 MPa. After the reaction is completed, it is cooled to room temperature, liquid in the reactor is centrifuged, and product is quantitatively analyzed by GC. The furfural conversion rate on Pt/Cu—Zn(Al)(Zr)O catalyst is measured to be 100%, and the selectivity to cyclopentanone is 92%.

Embodiment 3

Step A: $Cu(NO_3)_2 \cdot 3H_2O$ (20 mmol), $Zn(NO_3)_2 \cdot 6H_2O$ (36 mmol), $Al(NO_3)_3 \cdot 9H_2O$ (12 mmol), and $ZrO(NO_3)_2 \cdot 6H_2O$ (6 mmol) are dissolved in 200 mL deionized water as solution A, NaOH (0.156 mol), $Na_2CO_3$ (0.024 mol) are dissolved into 200 mL deionized water as solution B. Subsequently, at a constant pH (10.0), solutions A and B are simultaneously added dropwise to a four-necked flask containing 200 mL of deionized water. After crystallization at 65° C. for 12 hours, the solid is filtered, washed with deionized water several times until the filtrate is neutral, and then dried overnight at 80° C. to obtain a CuZnAlZr-LDHs sample.

Step B: add the CuZnAlZr-LDHs synthesized in step A into a tube furnace, under $H_2$ atmosphere (40 mL min$^{-1}$), raise the temperature from room temperature to 450° C. at a rate of 2° C. min$^{-1}$ and maintained for 2 hours, to obtained Cu—Zn(Al)(Zr)O. Take 1 g reduced Cu—Zn(Al)(Zr)O, liquid-seal it with 5 mL deionized water with oxygen removed, pour it into a round bottom flask, and add $Pt^{2+}$ solution under vigorous stirring and $N_2$ protection. After that, replacement reaction is proceeded with a reflux condenser at 100° C. under vigorous stirring for 2 hours. The mud-like substance separated by centrifugation is washed three times with deionized water, and dried in vacuum at 40° C. for 24 hours.

A Pt/Cu—Zn(Al)(Zr)O catalyst is thus prepared. The actual loading of Pt is 0.1%, the actual loading of Cu is 17%, and particle size of the metal center is 2-20 nm.

The Pt/Cu—Zn(Al)(Zr)O catalyst obtained in embodiment 3 is used to catalyze the furfural hydro-conversion. Add 0.5 g of furfural, 0.03 g catalyst, 10 mL ultrapure water to the lining of autoclave, install the autoclave, fill $H_2$ from the air inlet, replace the air in autoclave 5 times, then fill with 0.1 MPa $H_2$, seal the autoclave. The autoclave is heated to a preset temperature. The pressure is about 0.5 MPa at 160° C., and the timing is started. The reaction is continued for 10 hours. During the process, $H_2$ is continuously replenished to 0.5 MPa. After the reaction is completed, it is cooled to room temperature, liquid in the reactor is centrifuged, and product is quantitatively analyzed by GC. The furfural conversion rate on Pt/Cu—Zn(Al)(Zr)O catalyst is measured to be 100%, and the selectivity to cyclopentanone is 90%.

Experimental Control 1

Step A: $Cu(NO_3)_2 \cdot 3H_2O$ (14 mmol), $Zn(NO_3)_2 \cdot 6H_2O$ (42 mmol), $Al(NO_3)_3 \cdot 9H_2O$ (12 mmol), and $ZrO(NO_3)_2 \cdot 6H_2O$ (6 mmol) are dissolves in 200 mL deionized water as solution A, and NaOH (0.156 mol), $Na_2CO_3$ (0.024 mol) are dissolved into 200 mL deionized water as solution B. At a constant pH (10.0), solutions A and B are simultaneously added dropwise to a four-necked flask containing 200 mL of deionized water. After crystallization at 65° C. for 12 hours, the solid is filtered, washed with deionized water several times until the filtrate is neutral, and dried overnight at 80° C. to obtain a CuZnAlZr-LDHs sample.

Step B: add the CuZnAlZr-LDHs synthesized in step A into a tube furnace, raise the temperature at a rate of 2° C. min$^{-1}$ from room temperature to 450° C. and maintained for 2 hours under $H_2$ (40 mL min$^{-1}$) atmosphere, Cu—Zn(Al)(Zr)O is thus obtained.

The Cu—Zn(Al)(Zr)O catalyst is prepared and used as the control. The actual loading of Cu is 11%, and the center particle size of the metal is 2-20 nm.

The Cu—Zn(Al)(Zr)O catalyst obtained in Experimental control 1 is used to catalyze the furfural hydro-conversion. Add 0.5 g of furfural, 0.03 g catalyst, 10 mL ultrapure water to the lining of autoclave, install the autoclave, fill $H_2$ from the air inlet, replace the air in autoclave 5 times, then fill with 0.1 MPa $H_2$, seal the autoclave. The autoclave is heated to a preset temperature. The pressure is about 0.5 MPa at 160° C., and the timing is started. The reaction is continued for 10 hours. During the process, $H_2$ is continuously replenished to 0.5 MPa. After the reaction is completed, it is cooled to room temperature, liquid in the reactor is centrifuged, and product is quantitatively analyzed by GC. The furfural conversion rate on the Cu—Zn(Al)(Zr)O catalyst is measured to be 24%, and the selectivity to cyclopentanone is 9%.

It can be seen by comparing the outcomes of the embodiments and controlled experiment that the Pt/Cu catalyst has a superior function of hydrogenation of furfural to produce cyclopentanone.

What is claimed is:
1. A catalyst for preparing cyclopentanone by efficiently catalyzing the conversion of furfural, comprising: uniformly dispersed metal active center nanoparticles and an oxide obtained by calcination of layered double hydroxides

(LDHs), wherein the metal active center comprises single atom Pt/Cu alloy, wherein Pt atom is loaded in situ onto Cu surface.

2. The catalyst according to claim 1, wherein the Cu content of the metal active center in the catalyst is 5-30 wt %, the Pt content is 0.01-3 wt %, and the particle size of the single atom Pt/Cu alloy in the metal activity center is 2-20 nm.

3. The catalyst according to claim 1, wherein the Cu content of the metal active center in the catalyst is 8-20 wt %, the Pt content is 0.05-1 wt %, and the particle size of the single atom Pt/Cu alloy in the metal activity center is 2-10 nm.

4. A method for preparing the catalyst of claim 1, comprising:
obtaining a Cu-containing catalyst precursor by using LDHs as a precursor and performing a reduction reaction in a H2 atmosphere;
reacting with $Pt^{2+}$; and
washing and drying to obtain the catalyst comprising the single atom Pt/Cu alloy metal active center.

5. The method according to claim 4, further comprising:
reducing the Cu-containing catalyst precursor in a H2 atmosphere, with a reduction temperature at 400-650° C., and a reduction time from 5 minutes to 6 hours.

6. The method according to claim 5, further comprising:
selecting $Zn^{2+}$ or/and $Mg^{2+}$ as a divalent cation of the LDHs lattice of the Cu-containing LDHs precursor, selecting $Al^{3+}$ as a trivalent cation of the LDHs lattice of the Cu-containing LDHs precursor, wherein the metal active center ion inside the lattice is $Cu^{2+}$; the molar ratio between the divalent cation $Zn^{2+}$ or/and $Mg^{2+}$ of the LDHs lattice and the metal active center ion $Cu^{2+}$ inside the lattice is (0-10): 1, the divalent cation $Zn^{2+}$ or/and $Mg^{2+}$ of the LDHs lattice is not 0, and the molar ratio between all the divalent metal cations of the LDHs lattice $Zn^{2+}$, $Mg^{2+}$, $Cu^{2+}$ and all trivalent metal cations of the LDHs lattice is in the range of (2-5): 1.

7. The method according to claim 6, wherein when preparing the Cu-containing catalyst precursor using hydrotalcite as the precursor, the LDHs precursor also contains tetravalent cations in the LDHs lattice, the tetravalent cations are selected as $Zr^{4+}$, and the molar ratio of $Zr^{4+}$ to the trivalent cation $Al^{3+}$ is (0.1-1): 1.

8. The method according to claim 4, further comprising:
after reduction by $H_2$, sealing the Cu-containing catalyst precursor with de-oxygenated deionized water;
under stirring and $N_2$ protection, adding a $Pt^{2+}$ solution dropwise to the liquid-sealed Cu-containing catalyst precursor, and reacting at 90-120° C. for 1-3 hours; and
separating, washing, and drying to obtain the catalyst.

9. A method of using the catalyst of claim 1 to catalyze the conversion of furfural to produce cyclopentanone, further comprising:
reacting at the temperature of 120 to 250° C., under the pressure of 0.1 to 5 MPa, wherein the reaction time being 0.5 to 24 hours, and the reaction solvent being ultrapure water.

10. The method according to claim 9, further comprising:
reacting in a reactor, replacing air inside the reactor with hydrogen and maintaining appropriate pressure, the mass fraction of the substrate furfural being 1-20 wt %, the reaction temperature being 120-250° C., and the reaction pressure being 0.1-5 MPa, the reaction time being 0.5-24 hours, and the reaction solvent being ultrapure water.

11. A method for preparing the catalyst of claim 2, comprising:
obtaining a Cu-containing catalyst precursor by using LDHs as a precursor and performing a reduction reaction to a $H_2$ atmosphere;
reacting with $Pt^{2+}$; and
washing and drying to obtain the catalyst comprising the monatomic PT/Cu metal active center.

12. The method according to claim 11, further comprising:
reducing the Cu-containing catalyst precursor $H_2$ atmosphere, with a reduction temperature at 400° C. to 650° C., and a reduction time from 5 minutes to 6 hours.

13. The method according to claim 12, further comprising:
selecting $Zn^{2+}$ or/and $Mg^{2+}$ as a divalent cation of the LDHs lattice of the CU-containing LDHs precursor, selecting $Al^{3+}$ as a trivalent cation of the LDHs lattice of the $Cu^{2+}$; the molar ration between the divalent cation $Zn^{2+}$ or/and $Mg^{2+}$ of the LDHS lattice and the metal active $Cu^{2+}$ inside the lattice is (0-10):1, the divalent cation $Zn^{2+}$ or/and $Mg^{2+}$ of the LDHs lattice is not 0, and the molar ratio between all the divalent metal cations of the LDHs lattice $Zn^{2+}$, $Mg^{2+}$, $Cu^{2+}$ and all trivalent metal cations of the LDS lattice is in the range of (2-5):1.

14. The method according to claim 13, wherein when preparing the Cu-containing catalyst precursor using hydrotalcite as the precursor, the LDHs precursor also contains tetravalent cations in the LDHs lattice, the tetravalent cations are selected as $Zr^{4+}$, and the molar ratio of $Zr^{4+}$ to the trivalent cation of $Al^{3+}$ is (0.1-1):1.

15. The method according to claim 11, further comprising:
after reduction by $H_2$, sealing the Cu-containing catalyst precursor with de-oxygenated deiodized water;
under stirring and $N_2$ protection, adding the $Pt^{2+}$ solution dropwise to the liquid-sealed Cu-containing catalyst precursor, and reacting at 90-120° C. for 1-3 hours; and
separating, washing and drying to obtain the catalyst.

16. A method of using the catalyst of claim 2 to catalyze the conversion of furfural to prepare cyclopentanone, further comprising;
reacting at the temperature of 120 to 250° C., under the pressure of 0.1 to 5 MPa, wherein the reaction time being 0.5 to 24 hours, and the reaction solvent being ultrapure water.

17. The method according to claim 16, further comprising:
reacting in a reactor, replacing air inside the reactor with hydrogen and maintaining appropriate pressure, the mass fraction of the substrate furfural being 1-20 wt %, the reaction temperature being 120-250° C., and the reaction pressure being 0.1-5 MPA, the reaction time being 0.5-24 hours, and the reaction solvent being ultrapure water.

18. A method of preparing the catalyst of claim 3, comprising:
obtaining a Cu-containing catalyst precursor by using hydrotalcite as a precursor and performing a reduction reaction in a $H_2$ atmosphere;
reacting with $Pt^{2+}$; and
washing and drying to obtain the catalysts comprising the single atom Pt/Cu alloy metal active center.

19. The method according to claim 18, further comprising:
    reducing the Cu-containing catalyst precursor in a $H_2$ atmosphere, with a reduction temperature at 400-500° C., and a reduction time of 5 minutes to 6 hours.

20. The method according to claim 19, further comprising:
    selecting $Zn^{2+}$ or/and $Mg^{2+}$ as a divalent cation of the LDHs lattice of the CU-containing LDHs precursor, Selecting $Al^{3+}$ as a trivalent cation of the LDHs lattice of the Cu-containing LDHs precursor, wherein the metal active center ion inside the lattice is $Cu^{2+}$; the molar ratio between the divalent cation $Zn^{2+}$ or/and $Mg^{2+}$ of the LDHs lattice and the metal active center ion $cu^{2+}$ inside the lattice is (0-10):1, the divalent cation $Zn^{2+}$ or/and $Mg^{2+}$ of the LDHs lattice is not 0, and the molar ratio between all the divalent metal cations of the LDHs lattice $Zn^{2+}$, $Mg^{2+}$, $Cu^{2+}$ and all trivalent metal cations of the LDHs lattice is in the range of (2-5):1.

\* \* \* \* \*